(12) United States Patent
De Jong et al.

(10) Patent No.: US 8,293,873 B2
(45) Date of Patent: Oct. 23, 2012

(54) COMBINATION OF AMINO ACID SOLUTION AND A GELATIN DERIVATIVE FOR INHIBITING RENAL UP-TAKE

(75) Inventors: Marion De Jong, Vlaardingen (NL); Eric P. Krenning, Rotterdam (NL); Edgar Rolleman, Roosendaal (NL)

(73) Assignee: BioSynthema Inc., St. Louis, MO (US)

( * ) Notice: Subject to any disclaimer, the term of this patent is extended or adjusted under 35 U.S.C. 154(b) by 403 days.

(21) Appl. No.: 12/303,090

(22) PCT Filed: May 31, 2007

(86) PCT No.: PCT/EP2007/004914
§ 371 (c)(1),
(2), (4) Date: Jul. 16, 2009

(87) PCT Pub. No.: WO2007/137871
PCT Pub. Date: Dec. 6, 2007

(65) Prior Publication Data
US 2009/0318330 A1    Dec. 24, 2009

(30) Foreign Application Priority Data
May 31, 2006  (EP) .................................... 06076133

(51) Int. Cl.
*A61K 38/17*  (2006.01)
*A61K 38/00*  (2006.01)

(52) U.S. Cl. ......................................... 530/354; 514/1.1

(58) Field of Classification Search ........................ None
See application file for complete search history.

(56) References Cited

FOREIGN PATENT DOCUMENTS

| EP | 6076133 | 5/2006 |
|----|---------|--------|
| WO | WO 96/29087 | 9/1996 |
| WO | WO 01/05383 | 1/2001 |

OTHER PUBLICATIONS

De Jong et al.—"Inhibition of Renal Uptake of Indium-111-DTPA-Octreotide in Vivo", The Journal of Nuclear Medicine, vol. 37, No. 8, Aug. 1996, pp. 1388-1392, XP-000978763, ISSN: 0161-5505.

Bernard et al.—"D-Lysine Reduction of Indium-111 Octreotide and Yttrium-90 Octreotide Renal Uptake", The Journal of Nuclear Medicine, vol. 38, No. 12, Dec. 1997, pp. 1929-1933, XP-000946462, ISSN: 0161-5505.

Jamar et al.—"$^{86}$Y-DOTA$^0$-D-Phe$^1$-Tyr$^3$-octreotide (SMT487)—a phase 1 clinical study: pharmacokinetics, biodistribution and renal protective effect of different regimens of amino acid co-infusion", European Journal of Nuclear Medicine and Molecular Imaging, vol. 30, No. 4, Apr. 2003, pp. 510-518, XP-002405403, ISSN: 1619-7070.

Van Eerd et al.—"Gelatin-Based Plasma Expander Effectively Reduces Renal Uptake of $^{111}$In-Octreotide in Mice and Rats", The Journal of Nuclear Medicine, vol. 47, No. 3, Mar. 2006, pp. 528-533, XP-008070846, ISSN: 0161-5505.

Vegt et al.—"Renal Uptake of Radiolabeled Octreotide in Human Subjects Is Efficiently Inhibited by Succinylated Gelatin", The Journal of Nuclear Medicine, vol. 47, No. 3, Mar. 2006, pp. 432-436, XP-008070847, ISSN: 0161-5505.

Rolleman et al., "Safe and Effective Inhibition of Renal Uptake of Radiolabelled Octreotide by a Combination of Lysine and Arginine," European Journal of Nuclear Medicine and Molecular Imaging, Article, Jan. 2003, pp. 9-15, vol. 30, No. 1.

Barone et al., "Endocytosis of the Somatostatin Aralogue, Octreotide, by the Proximal Tubule-Derived Opossum Kidney (OK) Cell Line", Abstract only, pp. 2, (found in Kidney Int., Mar. 2005, pp. 969-976, vol. 67 No. 3.

De Jong et al., "Megalin is Essential for Renal Proximal Tubule Reabsorption of 111In-DTPA-Octreotide", The Journal of Nuclear Medicine, Oct. 2005, pp. 1696-1700, vol. 46, No. 10.

Rolleman et al., "Inhibition of Kidney Uptake of Radiolabeled Somatostatin Analogs: Amino Acids or Gelofusine?", The Journal of Nuclear Medicine, Oct. 2006, pp. 1730-1731, vol. 47, No. 10.

Van Eerd et al., "Reply to Rolleman et al. 'Inhibition of Kidney Uptake of Radiolabeled Somatostatin Analogs: Amino Acids or Gelofusine?'", The Journal of Nuclear Medicine, Oct. 2006, p. 1731, vol. 47, No. 10.

*Primary Examiner* — Suzanne M Noakes
(74) *Attorney, Agent, or Firm* — Thompson Coburn LLP

(57) ABSTRACT

The invention relates to a combination of a solution of a gelatin derivative and at least one amino acid, if desired in the form of a pharmaceutically acceptable salt or carboxylic acid derivative, for inhibiting renal uptake of substances, that are potentially damaging for the kidneys, in a living being.

24 Claims, 3 Drawing Sheets

COMBINATION OF AMINO ACID SOLUTION AND A GELATIN DERIVATIVE FOR INHIBITING RENAL UP-TAKE

BACKGROUND OF THE INVENTION

The present invention relates to the use of a solution of a gelatin derivative in combination with at least one amino acid, if desired in the form of a pharmaceutically acceptable salt or carboxylic acid derivative, for the preparation of a composition for inhibiting renal uptake of substances, that are potentially damaging for the kidneys, in a living being.

Radionuclide labeled peptides and also monoclonal anti-bodies or their fragments and other compounds like certain antibiotics or chemotherapeutic agents undergo undesired renal uptake and cellular retention leading to a high kidney radiation dose or concentration. Increased amounts of protein or raised doses of radiation or toxic substances in the kidneys may eventually lead to kidney damage.

In the patent publication EP 0094378 (PCT/EP00/06917) it has been described that co-administration of non-target substances, like lysine in combination with arginine, can reduce non-target kidney retention of immunoconjugates, metabolites thereof and other substances that are potentially damaging to the kidneys, such as defined above.

Recently it was published that the gelatin-based plasma-expanders Gelofusine® (B. Braun, Germany) and Haemaccel® result in tubular proteinuria. Such gelatine-based solutions are used in clinical medicine in hemorraghic and septic shock to control blood pressure levels, as well a in the post-surgical situation. Gelofusine is a synthetic colloidal solution based on bovine bone-derived gelatin, and may be considered as a gelatine-based plasma expander. Haemaccel is a synthetic colloidal solution of urea cross linked degraded gelatin. It was also published that Gelofusine could successfully been applied to reduce kidney uptake of radiolabeled octreotide to a level comparable to that of lysine. At present it is not clear by what mechanism gelatin-based plasma expanders inhibit kidney uptake of radiolabeled octreotide.

BRIEF SUMMARY OF THE INVENTION

It has now been found, that the combination of a solution of a gelatin derivative and an amino acid solution, in general, can be useful in reducing the kidney uptake and retention of all radiolabelled peptides, that are cleared through the kidneys. The term gelatin derivative should be understood to comprise all gelatin derivatives that are soluble in water. Suitable examples of aqueous solutions of such gelatin derivatives are the above commercially available products Gelofusine and Haemaccel. More specifically, the combination of Gelofusine and a lysine can be used to reduce kidney retention of [$^{177}$Lu-DOTA$^0$,Tyr$^3$]octreotate (see Example 1 attached). This would impact current peptide radionuclide radiotherapy protocols in a way that higher tumor radiation doses can be achieved without harming the kidneys. In addition, this may not only account for combinations of L-lysine and Gelofusine, but also for combinations of Gelofusine and D-lysine or polylysine, and for combinations with a mixture of a lysine and a second amino acid, selected from arginine and ornithine, and for combinations with commercially available amino acid solutions.

The combinations mentioned may also be used to reduce kidney uptake and retention of other toxic compounds that undergo undesired renal uptake and cellular retention, like monoclonal anti-bodies or their Rents and other compounds like certain antibiotics or chemotherapeutic agents.

DETAILED DESCRIPTION OF THE INVENTION

Figure 1:
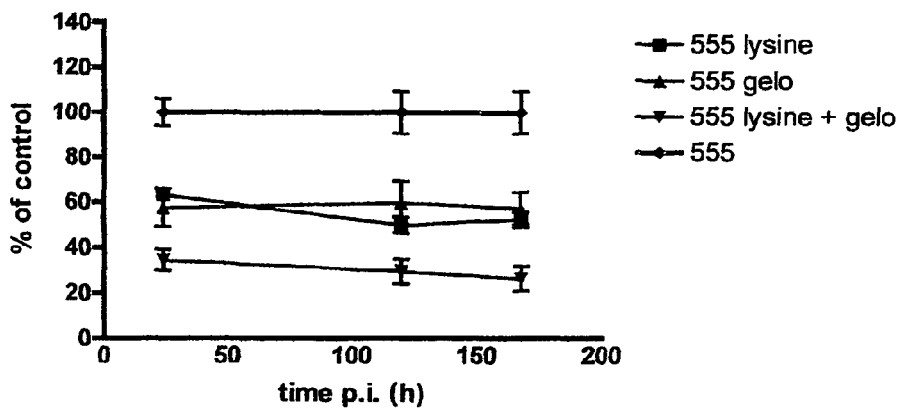
FIG. 1 shows reduction of kidney uptake of [$^{177}$Lu-DOTA$^0$, Tyr$^3$]octreotate by Gelofusine and lysine administration.

The invention therefore relates to the use of a solution of a gelatin derivative in combination with at least one amino acid for the preparation of a composition for inhibiting renal uptake of substances, that are potentially damaging for the kidneys, in a living being, wherein said at least one amino acid and said gelatin derivative are as defined hereinbefore.

In a preferred embodiment of the above combination the amount of the amino acid is between 150 and 700 mg per kg body weight, and the amount of the gelatin derivative between 50 and 250 mg per kg body weight of the being.

The invention further relates to a therapeutic composition for the inhibition of renal uptake of substances, that are potentially damaging for the kidneys and that are used for therapeutic or diagnostic purposes, in a living being, which composition comprises one or more pharmaceutically acceptable excipients, carriers and/or diluents and a combination of a gelatin derivative and at least one amino acid as defined hereinbefore.

The invention also relates to a method of inhibiting renal uptake of substances, that are potentially damaging for the kidneys, in a living being, by co-administration of a composition comprising at least one amino acid, if desired in the form of a pharmaceutically acceptable salt or carboxylic acid derivative, and a solution of a gelatin derivative, wherein said at least one amino acid and said gelatin derivative are as defined hereinbefore.

The invention will now be illustrated by the following specific Examples.

Example 1

Reduction of Kidney Uptake of [$^{177}$Lu-DOTA$^0$,Tyr$^3$] octreotate by the Combination of Gelofusine and Lysine as Visualised by NanoSPECT in Rats Aim: Peptide receptor radionuclide therapy (PRRT) using radiolabeled somatostatin analogs, kidney uptake of radiolabeled compound is the major dose-limiting factor. Positively charged amino acids are extensively used to reduce this uptake and to allow higher doses to be administered to patients. Recently it was shown that the gelatine-based plasma expander Gelofusine was capable to reduce kidney uptake of diagnostic doses of Octreoscan to a level comparable to that by lysine. We studied the effects of Gelofusine and lysine in therapeutic setting.

Method: Male Lewis rats (5-6 rats per group) were injected with 555 MBq [$^{177}$Lu-DOTA$^0$,Tyr$^3$]octreotate. For reduction of kidney rats were injected with 20 mg Gelofusine, 100 mg lysine or the combination. Kidney uptake was measured by SPECT scans with a four-elector multi-pinhole camera (NanoSPECT, Bioscan) at 24 h, 5 and 7 days pi. Kidney uptake was quantified by VOI analysis.

Results: At 24 h pi. kidney uptake of [$^{177}$Lu-DOTA$^0$,Tyr$^3$] octreotate was significantly reduced by both lysine and gelofusine (37%±6% and 43%±18% inhibition, respectively). The combination of gelofusine and lysine resulted in 65%±11% inhibition of kidney uptake (P<0.01 vs. lysine alone; P<0.05 vs. gelofusine alone). Five and seven days pi. inhibition levels were comparable to those 24 h pi.

Conclusion: Rat kidney uptake of radiolabeled somatostatin analogs can be monitored for a longer period in the same animal using animal SPECT. Gelofusine reduced kidney uptake of therapeutic doses [$^{177}$Lu-DOTA$^0$,Tyr$^3$]octreotate to a level comparable to that after lysine. The combination of these compounds led to a significantly stronger reduction than can be reached with lysine alone or with Gelofusine alone, whereas an overdose of lysine alone did not improve the reduction of the kidney uptake. During the experiment with the lysine-Gelofusine combination not any toxicity or other harmful side-effect has been observed. This may offer new possibilities in PRRT: FIG. 1

Example 2

Doubling the Gelofusine-Dose

In Example 1 the fixed Gelofusine dose was 20 mg, corresponding with 50-100 mg/kg. In the publication by Vegt et al. (Journal Nuclear Medicine 2006) a dose to humans was applied of 184 mg/kg. Both doses exert reductions of kidney uptake of radiolabeled somatostatin analogues that are comparable to the effects of lysine.

Figure 2:
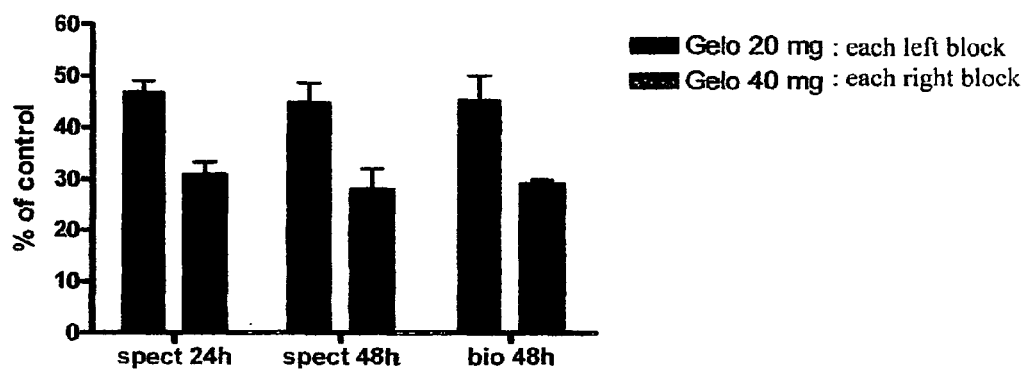
FIG. 2 shows reduction of kidney uptake of [$^{111}$In-DOTA$_0$, Tyr$^3$]octreotate by Gelofusine administration.
Figure 3:
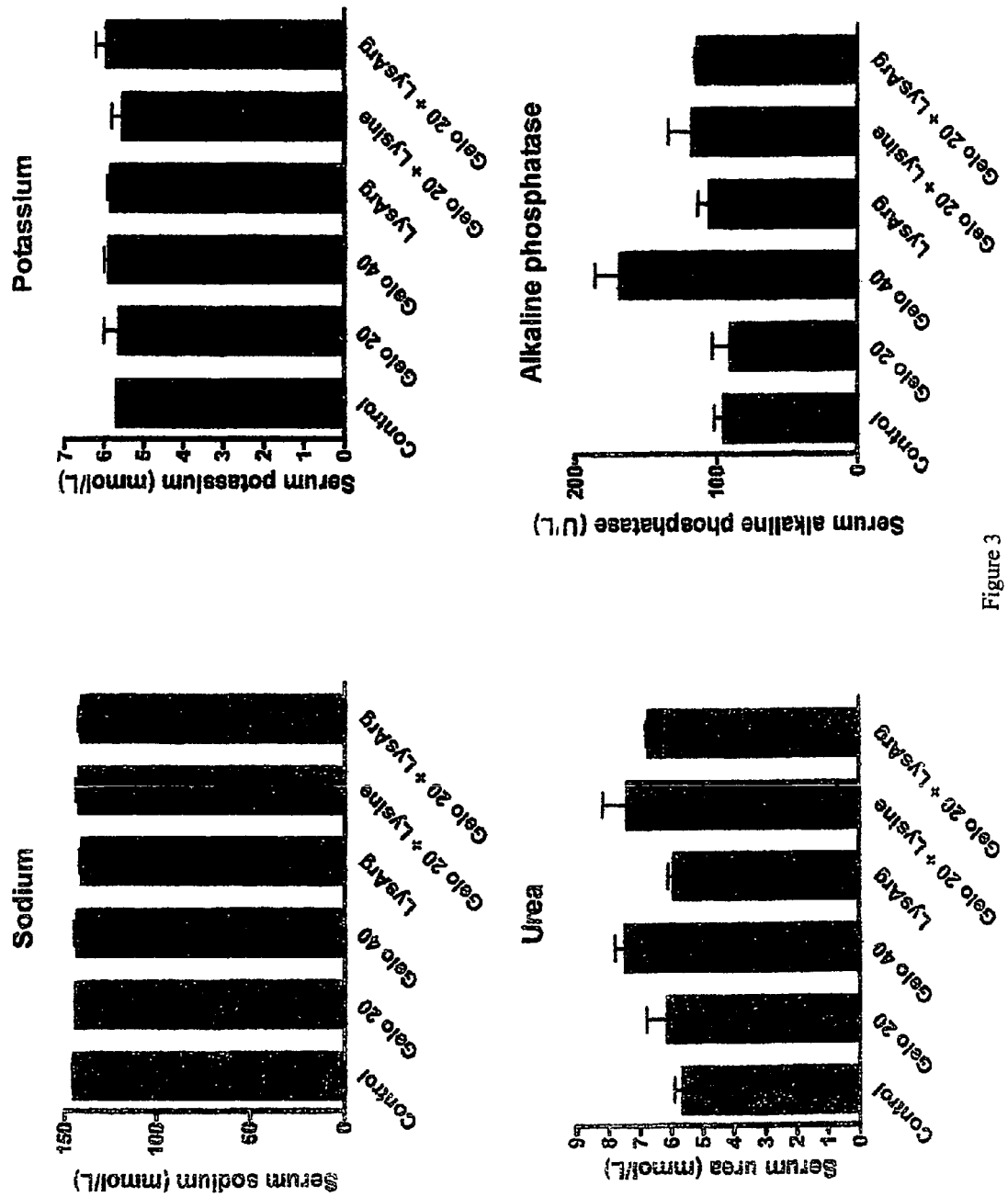
FIG. 3 shows serum levels of sodium, potassium, urea, and alkaline phosphatase in response to administration of Gelofusine.

In another experiment in rats the effects of 20 mg Gelofusine and 40 mg Gelofusine were tested on the kidney uptake of [$^{111}$DOTA$^0$,Tyr$^3$] octrotate. The kidney radioactivity was measured in vivo at 24 h and 48 h post injection with the small animal imaging camera, and after the last scan ex vivo determination of organ radioactivity was performed. As shown in FIG. 2, there is a clear trend that the 40 mg Gelofusine dose results in a greater kidney uptake reduction than 20 mg Gelofusine. However, the higher dose of Gelofusine resulted in an elevated alkaline phosphatase level, indicating liver damage (FIG. 3). Furthermore it is not clear if a double dose of Gelofusine has a comparable effect to the human kidney. It must be stressed that Vegt et al. (Journal Nuclear Medicine 2006) performed their studies in humans with a fixed dose of 184 mg/kg, which is already 2-fold higher than the dose applied to rats: FIGS. 2 and 3.

In this rat study no toxicity from the combination of Gelofusine plus LysArg or lysine was seen, as evidenced by normal potassium, sodium, alkaline phosphatase and urea concentrations (FIG. 3). Also, no histological changes were observed.

Example 3

Combination Gelofusine plus Lysine

Figure 4:
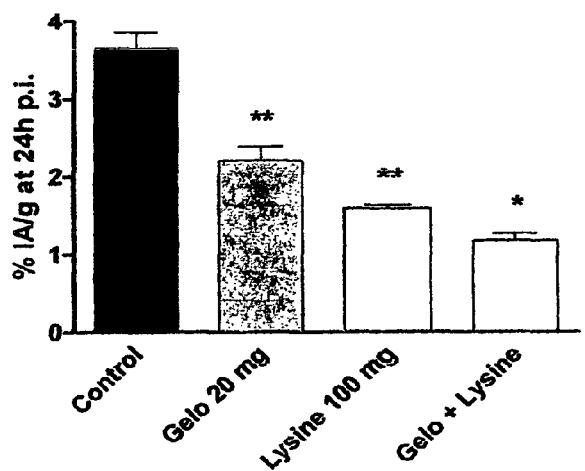
FIG. 4 shows reduction of kidney uptake of [$^{111}$In-DOTA$^0$, Tyr$^3$]octreotate by Gelofusine and lysine administration.

In Example 1 it was seen that the combination of Gelofusine plus lysine reduced the kidney uptake of [$^{177}$Lu-DOTA$^0$,Tyr$^3$]octreotate significantly better than lysine alone. In yet another experiment, at 24 hours post injection of [$^{111}$In-DOTA$^0$,Tyr$^3$]octreotate with or without Gelofusine (20 mg), or lysine (100 mg) or the combination of Gelofusine and lysine (20 mg and 100 mg, respectively) the kidney radioactivity content was measured. As shown in FIG. 4, the combination Gelofusine plus lysine again was significantly more efficient in reducing the kidney content of [$^{111}$In-DOTA$^0$, Tyr$^3$]octreotate than lysine alone or Gelofusine alone: FIG. 4.

Example 4

Combination Gelofusine Plus Lysine+Arginine

Figure 5:
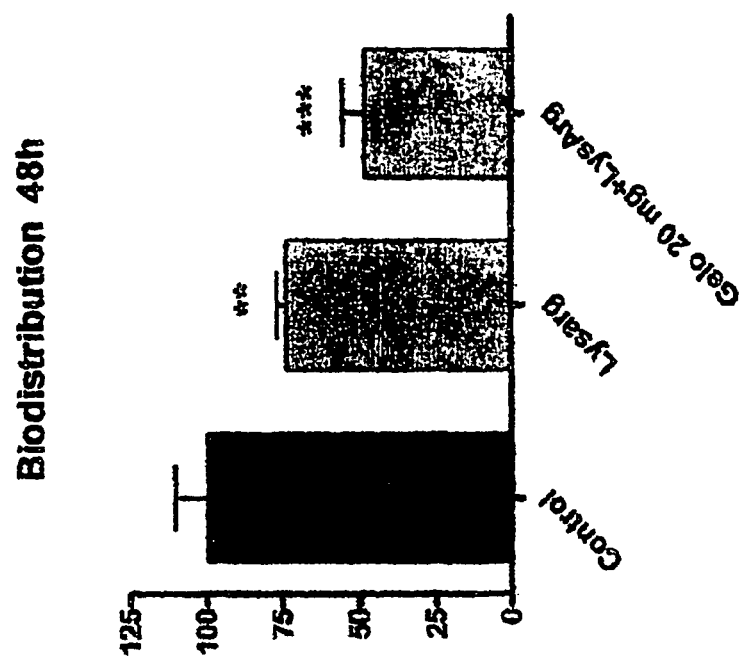
FIG. 5 shows reduction of kidney uptake of [$^{111}$In-DOTA$^0$, Tyr$^3$]octreotate by Gelofusine, lysine, and arginine administration.
Figure 5:
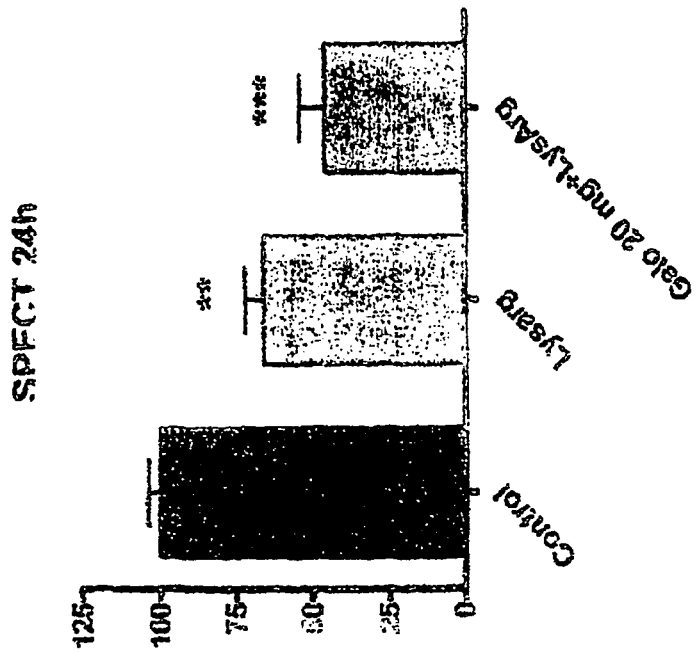

In another experiment testing was performed of the addition of Gelofusine to the LysArg solution, which is the standard solution used in the clinic for kidney protection during peptide receptor radionuclide therapy, consisting of 25 grams of lysine and 25 grams of arginine, dissolved in litre. The experimental protocol was identical to the above experiments: kidney radioactivity was measured 24 and 48 hours after injection of [$^{111}$In-DOTA$^0$, Tyr$^3$]octrotate with or without LysArg (1 mL, which consists of 25 mg lysine and 25 mg arginine) or the combination of Gelofusine (20 mg) plus LysArg (1 mL). Again, the combination was significantly more potent in inhibiting kidney uptake of [$^{111}$In-DOTA$^0$, Tyr$^3$]octreotate than LysArg alone: FIG. 5.

Example 5

Human Study

The addition of Gelofusine to the standard applied infusion of 25 grams of lysine+25 grams of arginine (LysArg) was investigated during 4 hours in a patient that was treated with high doses of [$^{177}$Lu-DOTA$^0$,Tyr$^3$]octreotate. A reduction of 25% was found by the combination Gelofusine+LysArg as compared to the infusion of LysArg alone. So, there is a distinct benefit of the combination versus LysArg alone.

The invention claimed is:

1. A therapeutic composition for the inhibition of renal uptake of substances that are potentially damaging for the kidneys and that are used for therapeutic or diagnostic purposes in a living being, comprising:
    a solution of a gelatin derivative;
    at least one amino acid; and
    at least one of a pharmaceutically acceptable excipient, carrier, diluent, and combinations thereof.

2. The composition of claim 1, wherein the composition includes a first quantity of the first amino acid in a range of about 150 milligrams to about 700 milligrams per kilogram body weight of a living being, and a second quantity of the gelatin derivative in a range of about 50 milligrams to about 250 milligrams per kilogram body weight of a living being.

3. The composition of claim 1, wherein the first amino acid is a lysine selected from the group consisting of D-lysine, L-lysine and polylysine.

4. The composition of claim 1, wherein the first amino acid is a lysine, wherein the composition further comprises a second amino acid selected from the group consisting of arginine and ornithine.

5. A method of preparing a composition for inhibiting renal uptake of a substance in a living being, comprising:
    combining a solution of a gelatin derivative with at least one amino acid.

6. The method of claim 5, wherein the at least one amino acid is in the form of a pharmaceutically acceptable salt or carboxylic acid derivative.

7. The method of claim 5, wherein the at least one amino acid is a lysine selected from the group consisting of D-lysine, L-lysine, and polylysine.

8. The method of claim 5, wherein the at least one amino acid is a mixture of a lysine and a second amino acid selected from the group consisting of arginine and ornithine.

9. The method of claim 5, wherein the gelatin derivative is a gelatin-based plasma expander.

10. The method of claim 9, wherein the gelatin-based plasma expander is GELOFUSINE®.

11. The method of claim 5, wherein the gelatin derivative is a synthetic colloidal solution of urea cross-linked degraded gelatin.

12. The method of claim 11, wherein the synthetic colloidal solution of urea cross-linked degraded gelatin is HAEMACCEL®.

13. The method of claim 5, wherein the composition includes a first quantity of the at least one amino acid in a range of about 150 milligrams to about 700 milligrams per kilogram body weight of the living being, and a second quantity of the gelatin derivative in a range of about 50 milligrams to about 250 milligrams per kilogram body weight of the living being.

14. The method of claim 5, further comprising combining at least one of a pharmaceutically acceptable excipient, carrier, diluent, and combinations thereof with the combination of the solution of the gelatin derivative and the at least one amino acid.

15. A method of inhibiting renal uptake of a substance in a living being, comprising:
   preparing a composition, wherein the composition includes:
   a solution of a gelatin derivative; and
   a first amino acid, wherein the first amino acid is in the form of a pharmaceutically acceptable salt or carboxylic acid derivative; and
   administering the composition to the living being.

16. The method of claim 15, wherein the first amino acid is a lysine selected from the group consisting of D-lysine, L-lysine and polylysine.

17. The method of claim 15, wherein the first amino acid is a lysine, wherein the composition further comprises a second amino acid selected from the group consisting of arginine and ornithine.

18. The method of claim 15, wherein the gelatin derivative is a gelatin-based plasma expander.

19. The method of claim 18, wherein the gelatin-based plasma expander is GELOFUSINE®.

20. The method of claim 15, wherein the gelatin derivative is a synthetic colloidal solution of urea cross-linked degraded gelatin.

21. The method of claim 20, wherein the synthetic colloidal solution of urea cross-linked degraded gelatin is HAEMACCEL®.

22. The method of claim 15, wherein the composition includes a first quantity of the first amino acid in a range of about 150 milligrams to about 700 milligrams per kilogram body weight of the living being, and a second quantity of the gelatin derivative in a range of about 50 milligrams to about 250 milligrams per kilogram body weight of the living being.

23. The method of claim 15, wherein the composition further comprises at least one of a pharmaceutically acceptable excipient, carrier, diluent, and combinations thereof.

24. The composition of claim 1, wherein the gelatin derivative is a gelatin-based plasma expander.

* * * * *